United States Patent [19]
Evans

[11] Patent Number: 6,145,370
[45] Date of Patent: Nov. 14, 2000

[54] LOADING MECHANISM FOR MACHINES ADAPTED TO TEST MATERIAL WEAR AND LUBRICATION PROPERTIES

[76] Inventor: Paul R. Evans, 5S342 Scott Rd., Big Rock, Ill. 60511

[21] Appl. No.: 09/220,743

[22] Filed: Dec. 23, 1998

[51] Int. Cl.[7] .................................................. G01N 19/02
[52] U.S. Cl. ........................................................ 73/7
[58] Field of Search ........................................ 73/7, 9, 10

[56] References Cited

U.S. PATENT DOCUMENTS

| | | |
|---|---|---|
| 2,106,170 | 1/1938 | Faville . |
| 2,110,288 | 3/1938 | Cornell . |
| 3,190,109 | 6/1965 | Faville . |

OTHER PUBLICATIONS

ASTM Standard, Standard Test Methods, pp. 309–318, No Date.

ASTM Standard, Standard Test Methods, pp. 61–65, No Date.

*Primary Examiner*—Robert Raevis
*Attorney, Agent, or Firm*—Keith Frantz

[57] ABSTRACT

A machine for testing material wear and lubrication properties between a bearing pin and opposing bearing blocks includes a wear-test loading apparatus comprising a guide mounted to the frame of the machine, a pair of bearing block holders slidably mounted to the guide, and a low-friction actuator such as a piston-type pneumatic mounted to the bearing block holders for movement there with and independently of the frame. The actuator piston rod is connected to the bearing block holder on one side of the pin adjacent the actuator, and the actuator housing is connected to the bearing block holder on the other side of the pin. When the actuator is pressurized, the piston and housing tend to separate under equal and opposite force due to the pressure in the actuator. This separation causes the bearing block holders to simultaneously slide on the guide and be drawn inwardly toward one another, and thus toward and into bearing contact with the pin, with equal and opposite force. An LVDT or other linear motion sensor may be mounted to detect the relative linear motion between the machine housing and at least on of the sliding bearing blocks. A torque-sensing apparatus may be mounted to detect the torque generated between the bearing blocks and the rotating test pin during the test. In this instance, the guide is rotatably mounted to the spindle housing to permit rotation of the entire bearing block, actuator unit about the axis of the pin during the test, and a force transducer is mounted between one of the bearing blocks and the frame of the machine to detect the torque generated during the test.

15 Claims, 8 Drawing Sheets

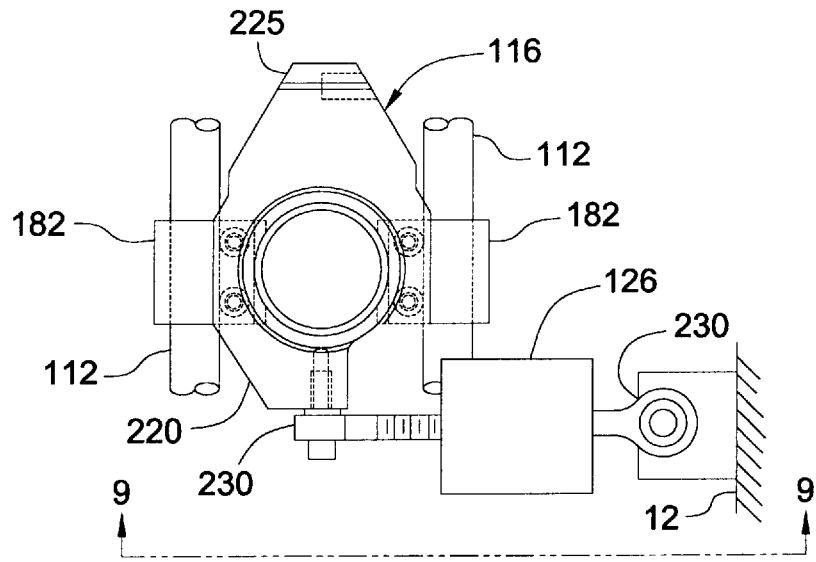
Fig. 8
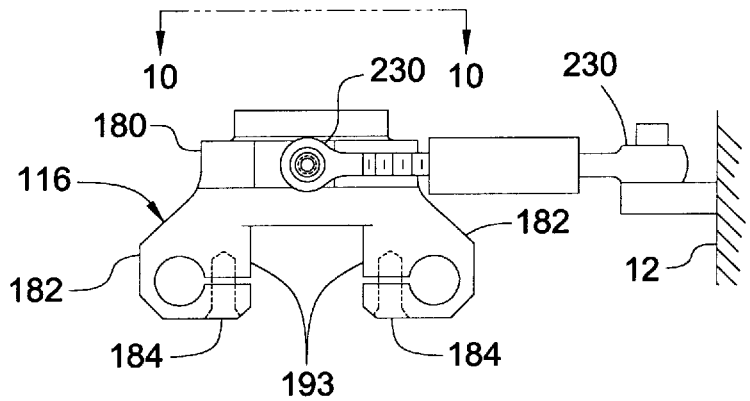
Fig. 9
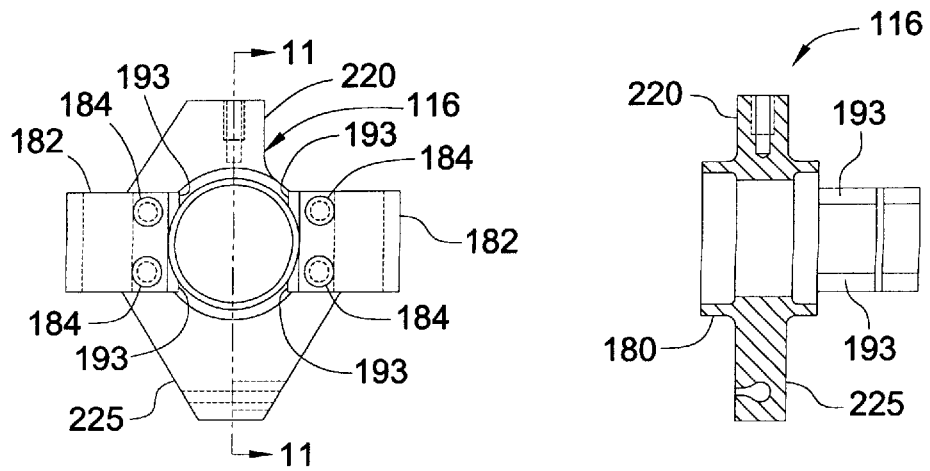
Fig. 10
Fig. 11

LOADING MECHANISM FOR MACHINES ADAPTED TO TEST MATERIAL WEAR AND LUBRICATION PROPERTIES

BACKGROUND OF THE INVENTION

This invention relates generally to machines adapted to test material wear and lubrication properties. More specifically, the invention relates to loading mechanisms for such machines such as of the type having wear specimens disposed on either side of a rotating pin, the loading mechanism being adapted to apply pressure between the wear specimens and the pin for wear and lubrication testing purposes.

One such test machine is disclosed in M. Cornell, U.S. Pat. No. 2,110,288, and certain associated test methods are disclosed in F. A. Faville, U.S. Pat. No. 2,106,170 and F. A. Faville, U.S. Pat. No. 3,190,109. Standardized tests for such machines are included in ASTM D 2670-88, Measuring Wear Properties of Fluid Lubricants; ASTM D 3233-93, Measurement of Extreme Pressure Properties of Fluid Lubricants; and ASTM D 2625-90, Endurance (Wear) Life and Load-Carrying Capacity of Solid Film Lubricants.

In conventional prior machines of this general type, loading jaws (a.k.a. bearing block holders) located on either side of the pin carry wear specimens (a.k.a. bearing blocks) formed with a V-shaped notches for receiving and establishing bearing contact with the pin. During testing, a loading or force application mechanism moves the jaws inwardly toward the pin to establish a desired contact loading or pressure condition between the bearing blocks and the rotating pin.

In such prior machines, an operator manually adjusts a ratcheting loading mechanism to move the jaws into contact with the pin and establish the desired loading condition. The pressure between the bearing blocks and the pin is related to the position of the jaws and the ratchet mechanism, therefore, the pressure between the pin and the bearing blocks decreases as wear occurs. Maintaining a relatively constant bearing pressure requires constant vigilance by the test operator, and adjustment of the ratchet mechanism during the test, typically requiring several adjustments during a 60 second test (see e.g., Faville, U.S. Pat. No. 3,190, 109, col. 4, lines 22–26). As a result, pressure loading conditions can vary substantially during a test, depending on the amount of wear and the operator's vigilance in watching for and correcting for changes in pressure due to the wear. Prior ratchet mechanisms of this type are also typically adapted for conducting a test under increasing loading conditions, however, the construction of such prior mechanisms, including relatively high hysteresis, generally preclude accurate, consistent, or controlled decrease of loading pressure during the same test and depending on the starting point of the increasing load in the hysteresis curve, can result in unrepeatable test results. In addition, such prior machines are not easily adapted for, and generally do not provide for measurement of wear during the test. These unfortunate characteristics and deficiencies of prior machines of this type are well known and documented in the prior art.

SUMMARY OF THE INVENTION

The general aim of the present invention is to provide new and improved apparatus for applying pressure between wear specimens and the rotating pin of a machine adapted to test material wear and lubrication properties, the apparatus being adapted to automatically provided for controlled loading conditions, including maintain a constant loading condition, if desired, between the pin and the wear specimens as the pin and/or the specimens experience wear, independent of the wear during the test, thus eliminating the need for constant vigilance and participation of a test operator, and providing for enhanced repeatability of test results.

Other objectives of the invention include:

1. providing a loading mechanism with substantially less hysteresis when compared with prior loading mechanisms utilized;
2. providing for greater load control accuracy as compared with prior machines of the same general type;
3. providing a mechanism that is capable of automatically increasing and decreasing the pressure between the pin and the wear specimens in a controlled, accurate, and consistent manner during testing;
4. providing for increased load range capability for the testing of wear and lubrication properties;
5. providing for linear measurement and recording of total wear during testing; and
6. providing for torque generated measurements during testing.

A detailed objective is to achieve the foregoing by providing a low friction, low hysteresis apparatus adapted to preferably apply direct, in-line linear pressure between the pin and the bearing blocks, independent of block position, and thus eliminating the error producing operation and non-linearities of prior machines and associated loading mechanisms.

These and other objectives and advantages of the invention will become more apparent from the following detailed description when taken in conjunction with the accompanying drawings.

Briefly, the loading apparatus of the present invention replaces the mechanical ratcheting loading apparatus of prior test machines with a low-friction actuator that provides predictable, controlled loading, independent of position, and that is uniquely mounted to insure equal pressure on both sides of the pin independent of position and wear. To this end, the bearing block holders are slidably mounted to guide rods that are connected fixed with respect to translation to the frame of the machine such that the bearing blocks may slide freely with respect to the frame, and thus freely with respect to the pin mounted in the machine. The preferred loading mechanism is a linear-acting actuator such as a pneumatic actuator with its piston rod connected to the bearing block holder on one side of the pin adjacent the actuator, and with its housing connected to the bearing block holder on the other side of the pin. When the actuator is pressurized, the piston and housing tend to separate under equal and opposite force due to the pressure in the actuator. This separation causes the bearing block holders to simultaneously slide on the guide rods and be drawn inwardly toward one another, and thus toward and into bearing contact with the pin, with equal and opposite force. With such an arrangement, testing is conducted under controlled, predictable, repeatable load conditions by simply controlling the pressure in the actuator. A preferred embodiment of the machine includes an LVDT or other linear motion sensor mounted so as to detect the relative linear motion between the machine housing and at least on of the sliding bearing blocks. Additionally, a preferred embodiment of the machine is equipped with a torque-sensing apparatus to detect the torque generated between the bearing blocks and the rotating test pin during the test. In this instance, the guide rods are rotatably mounted to the spindle housing to permit rotation of the entire bearing block, actuator unit about the axis of the pin during the test, and a force transducer is mounted between one of the bearing blocks and the frame of the machine to detect the torque generated during the test.

BRIEF DESCRIPTION OF THE DRAWINGS

FIG. 8 is a view of a torque sensing assembly as seen along the line 8—8 of FIG. 4.

FIG. 9 is a right side view of the torque assembly as seen generally along line 9—9 of FIG. 8.

FIG. 10 is a bottom view of a load pivot housing shown in FIGS. 8 and 9, and as seen along the line 10—10 of FIG. 9.

FIG. 11 is a cross-sectional view taken along the line 11—11 of FIG. 10.

Figure 1:
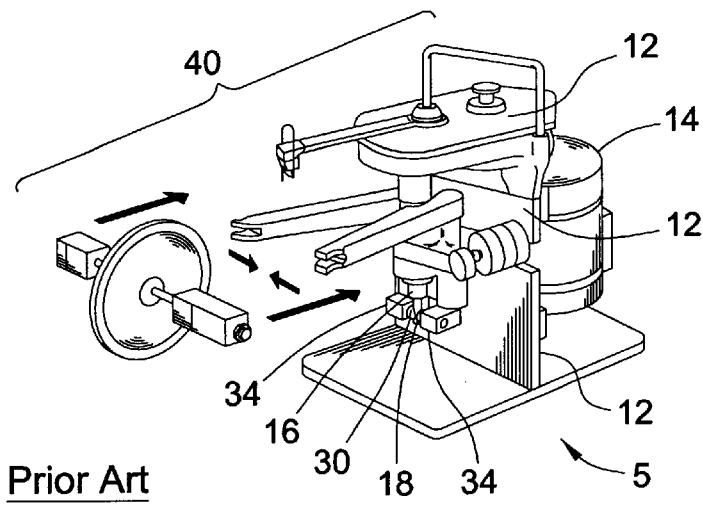
FIG. 1 is a view of a prior wear testing machine having a rotatable pin, and a ratchet wheel and lever arm apparatus for applying pressure to the pin such as generally disclosed in Cornell.

While the invention is susceptible of various modifications and alternative constructions, certain illustrated embodiments have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the invention.

DETAILED DESCRIPTION OF THE INVENTION

For purposes of illustration, the present invention is shown in the drawings as a loading apparatus 10 (FIG. 4) adapted for use with a bench test machine of the type commonly used in testing material and lubricant wear properties by applying opposing pressure from a pair of bearing blocks to a rotating pin. One such prior machine 5 (FIG. 1) is generally disclosed in M. Cornell, U.S. Pat. No. 2,110, 288. The basic construction and operation of such machines is well known, and will therefore be discussed herein only to the extent needed for understanding of the present invention. In the present instance, the ratchet mechanism loading arrangement of prior machines, such as the apparatus disclosed in Cornell, and as generally indicated at 40 (FIG. 1) in machine 5, is replaced with the improved loading apparatus 10 (FIG. 4) of the present invention.

Figure 2:
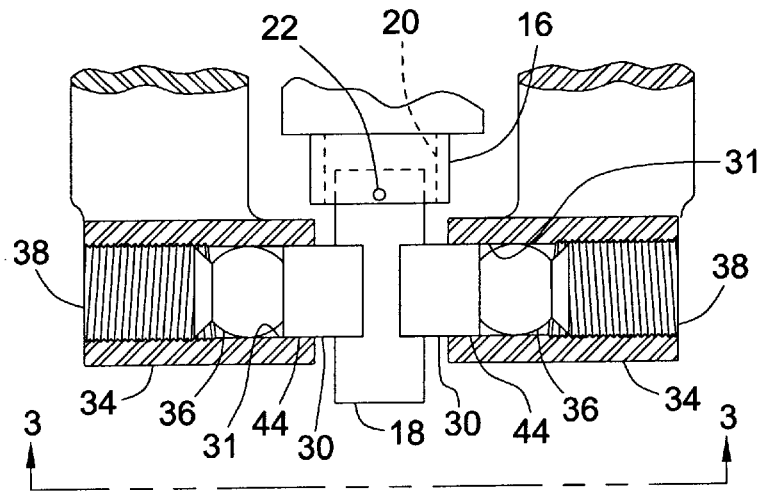
FIG. 2 is an enlarged fragmentary cross-sectional view of conventional loading jaw, bearing block and pin arrangement for testing material wear and lubrication properties.
Figure 3:
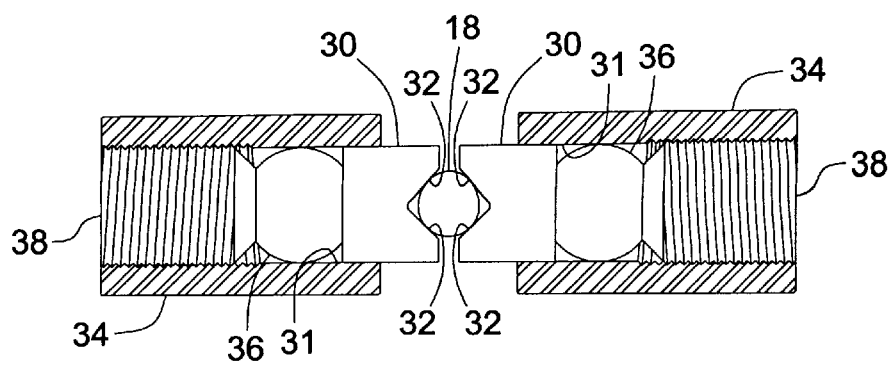
FIG. 3 is a fragmentary cross-sectional view taken substantially along the line 3—3 of FIG. 2.

In general, the test machine 5 includes a frame structure 12 (FIG. 1) and an electric motor 14 operably connected to a collar 16 for rotation of the collar about a vertical axis. Bearing pin 18 is slidably received into opening 20 (FIG. 2) in the collar, and is typically secured therein with shear pin 22 slidably extending through a transverse opening formed through the collar and through an aligned transverse opening formed through the upper end portion of the bearing pin 18. Wear specimens or bearing blocks 30 are formed with wear surfaces 32 (FIG. 3) which define substantially V-shaped notches facing one another for receiving the bearing pin 18 therebetween.

During normal operation of the test machine, i.e., during a typical wear or lubrication test, the bearing pin 18 is rotated by the electric motor 14, and a loading apparatus applies pressure between the wear specimens and the pin, resulting in line-bearing pressure or frictional contact between the stationary bearing surfaces 32 and the rotating bearing pin. Such tests are typically conducted either dry or with the bearing/wear surfaces immersed in a lubricant 35 (FIG. 4) contained in an oil cup 33. It is noted that, although line-bearing pressure of contact is referred to in the procedures, genuine line contact ceases and slight area contact results as soon as the bearing surfaces begin to wear.

The opposing bearing blocks 30 may be carried in opposing loading jaws 34 in a conventional manner, with the jaws operably connected to the load applying mechanism 10 as further discussed below. In this instance, the bearing blocks 30 are slidably carried in an opening 31 in the loading jaws, with a ball 36 and a set-screw 38 located in the opening 31 in each loading jaw to limit radial outward movement of the bearing blocks.

In accordance with the present invention, the apparatus 10 includes jaw holder assemblies 100, 110 (FIG. 4) disposed on either side of the pin 18 for carrying the loading jaws 34, and a linear load-generating actuator assembly 40 uniquely connected and adapted to apply controlled pressure between the bearing blocks 30 and the pin 18 independent of the wear experienced during a test. In preferred embodiments, and the actuator illustrated, is a pneumatic-type actuator to enable use of commonly available pressurized air sources, however, it will be apparent that the load-generating mechanism may be of other known construction such as a hydraulic actuator or other linear mechanical loading arrangement as herein contemplated within the scope of the present invention.

The actuator 40 shown is of generally conventional dual-acting, dual-area construction, and includes a housing 50, and a cap 52 provided with air inlet ports 51 and 53 communicating with annular air chambers 62 and 64, respectively, defined within the actuator, the cap being secured to the housing with bolts 49 angularly spaced about diameters thereof. A movable piston assembly 54 in the actuator is connected to a piston rod or load cylinder rod 55 such as with a piston load ring 37, threaded connection or other mechanical connecting means, and which extends through the base of the housing 50.

The actuator 40 shown is a two-stage actuator, providing for a high and low operating range. To this end, the piston assembly 54 includes a piston 56, outer and inner elastimeric rolling diaphragms 58 and 60, respectively, and outer and inner diaphragm retaining rings 59 and 61, respectively. The diaphragms are connected between (a) the housing 50 and the cap 52, and (b) the diaphragm retaining rings, as shown in FIG. 4, the diaphragm retaining rings being secured to the piston with screws or threaded bolts spaced about the diameters thereof.

With this arrangement, either the low pressure chamber 62, or both the low pressure chamber and high pressure chamber 64 may be utilized to actuate the piston. Air pressure provided to the low pressure chamber (through port 51) acts over the operative area provided by the diameter of the inner diaphragm 60, and air pressure provided to both chambers (through ports 51 and 53) act on the operative area provided by the diameter of the outer diaphragm 58. Such an arrangement allows for variable loading conditions by adjusting a standard air pressure regulator (not shown) connected to one or both of the ports upstream of the actuator, and allows an actuator of a specific size to be used with air sources of various pressure capacities for a range of loading conditions. It is noted that when using elastimeric rolling diaphragms as illustrated, the pressure in the low chamber 62 must be maintained greater than or equal to the pressure in the high chamber 64 to prevent the inner diaphragm from collapsing toward the cap 52, and it is contemplated that provision for such safeguard will either be provided upstream of the actuator, or through the use of a check/relief valve located, for example, in the side of the piston 54, and communicating between the high and low chambers to guard against the occurrence of such condition.

Figure 7:
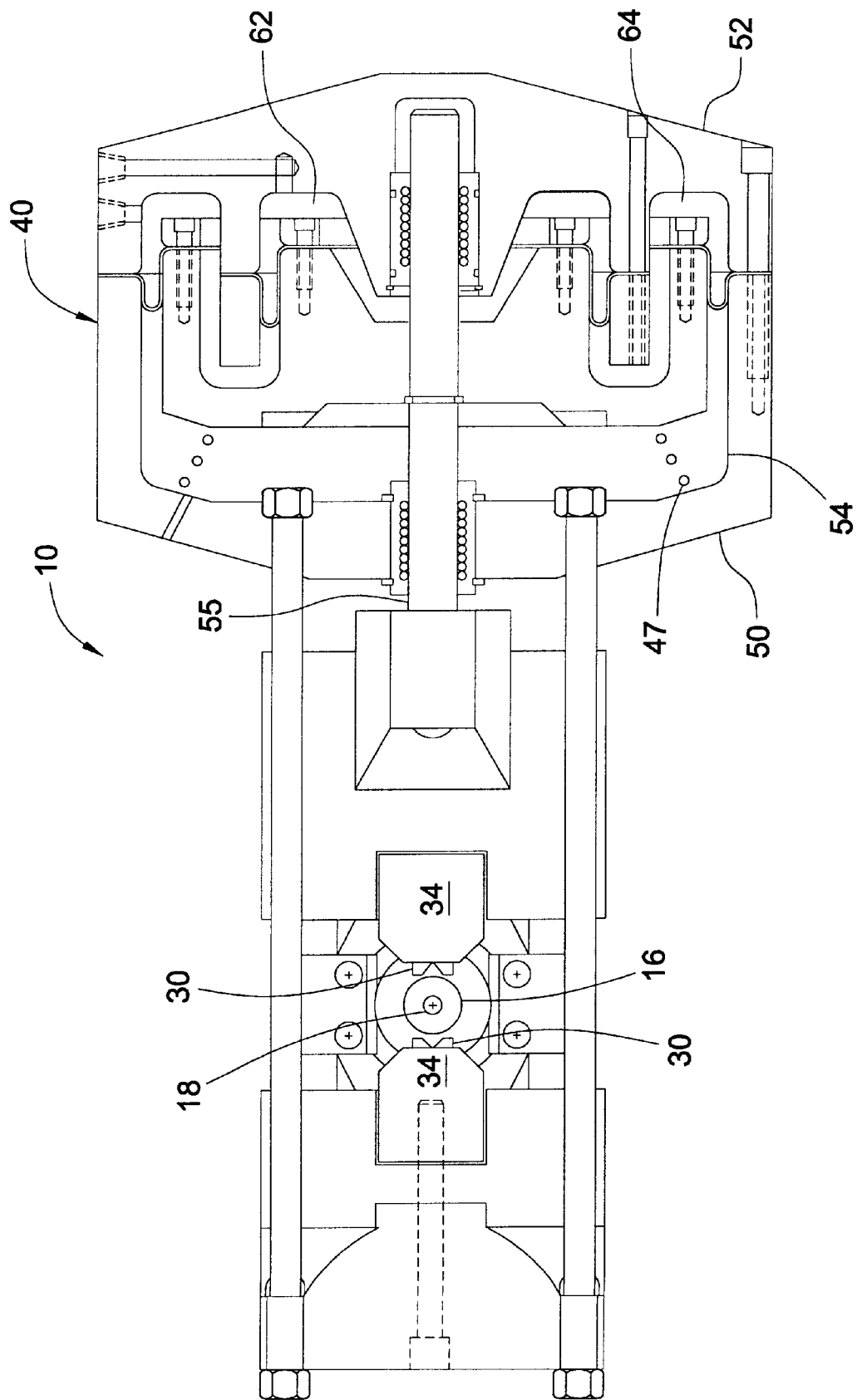
FIG. 7 is a view similar to FIG. 6 but showing the loading mechanism of the present invention moved to an unloaded position.

Advantageously, the loading arrangement of the invention, and as further discussed below, allows for greater load-test capacity between the bearing blocks 30 and the bearing pin 18 as compared with prior arrangements for the same size machine due to the ability to utilize high pressure pneumatic or hydraulic pressure sources. Further, a pneumatic actuator with rolling diaphragms provides for especially low friction and low hysteresis in the actuator, thus enabling enhanced resolution of load control during testing, and reduced error producing inaccuracies as compared with prior loading mechanisms utilized in material wear and lubricant testing machines. In further effort to keep the friction in the actuator to a minimum, the piston rod 55 is preferably supported for linear motion in linear ball bearings 57. In addition, the forward (left) chamber 66 of the actuator is vented to atmosphere at 61 to prevent pressure variations therein as the piston strokes, and a spring 47 may be optionally provided in the forward chamber for biasing the piston to automatically move to an unloaded position (such as is shown in FIG. 7) when air pressure is removed from the actuator.

Figure 4:
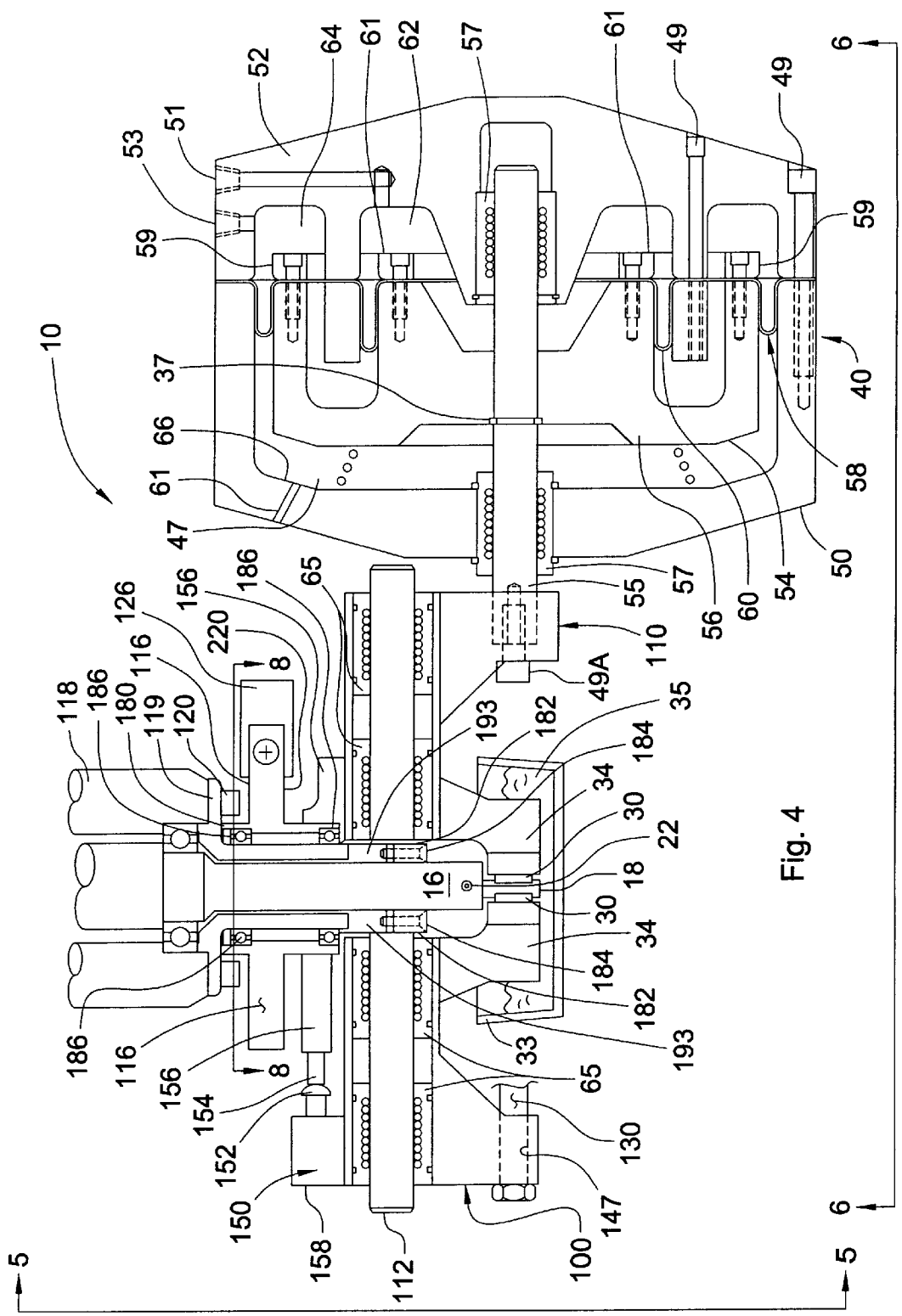
FIG. 4 is an enlarged front cross-sectional view of a loading mechanism for use in material wear and lubrication testing machines, and showing the unique aspects of the present invention.
Figure 5:
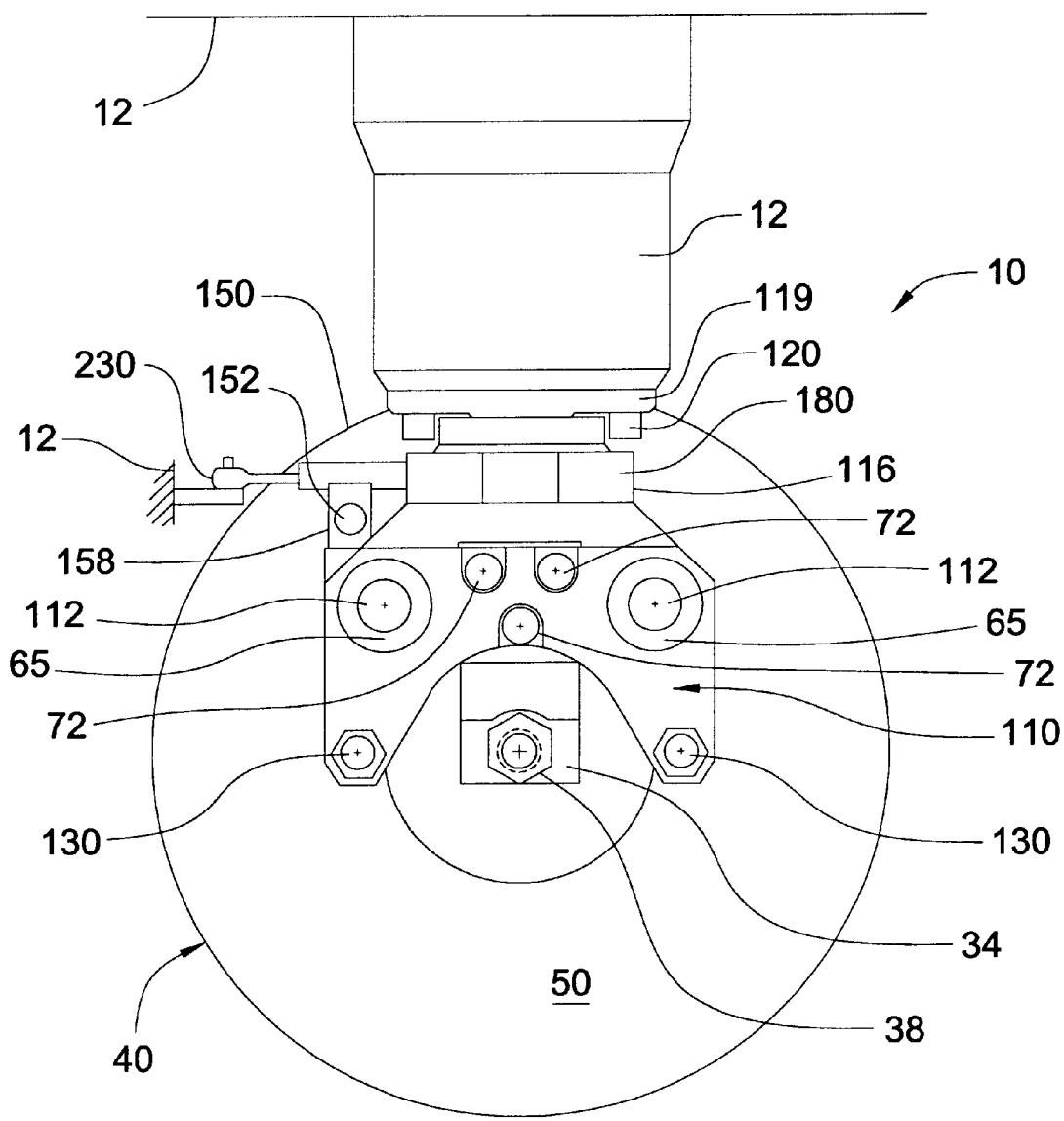
FIGS. 5 and 6 are left side and bottom views taken substantially along the lines 5—5 and 6—6, respectively, of FIG. 4.
Figure 12:
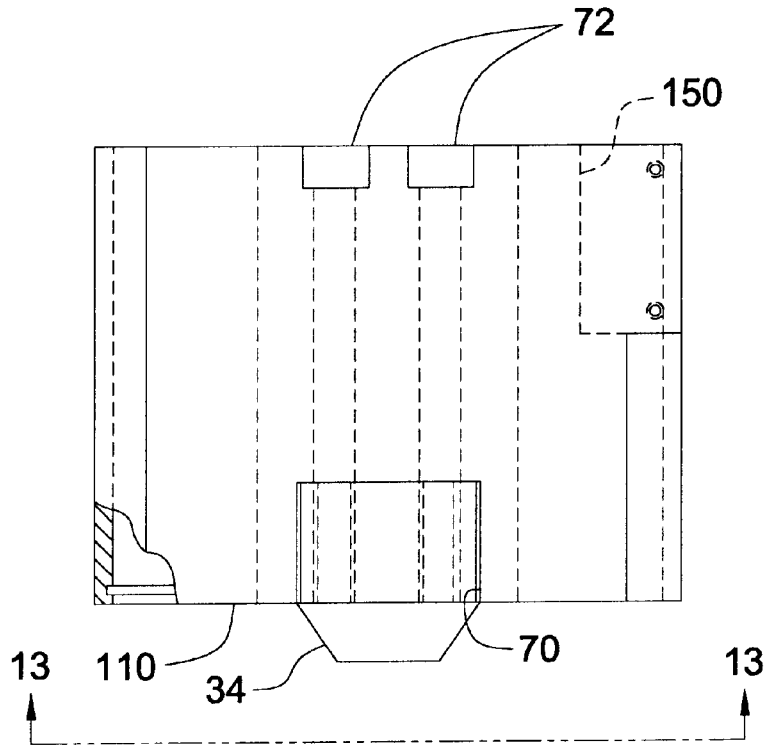
FIG. 12 is an enlarged top view of the left side jaw holder and jaw.
Figures 13, 14:
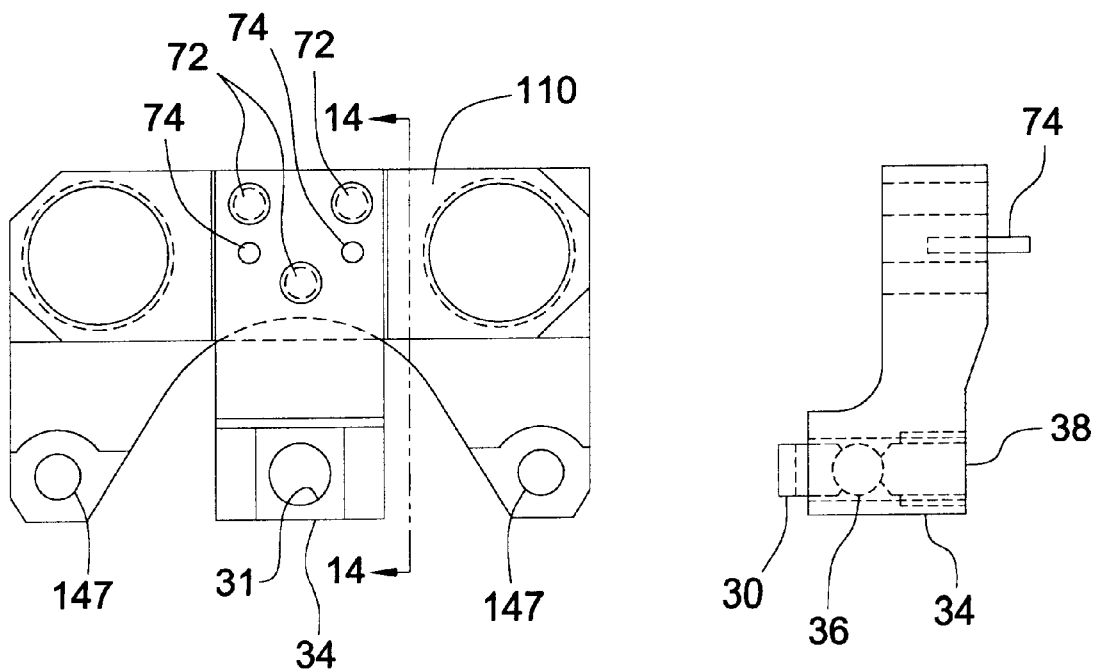
FIG. 13 is a view taken along the line 13—13 of FIG. 12.
FIG. 14 is a side view of a jaw as seen along the line 14—14 of FIG. 13.

The left and right jaw holder assemblies, 100 and 110, respectively, as viewed in FIG. 4, carry left and right jaws 34 for carrying the bearing blocks 30 as previously described. The jaws are slidably received into slots 70 (see FIGS. 6, 7, and 12–14) formed in the inner side portions (with respect to the bearing pin 18) of the jaw holders, and are retained in the slots by bolts 72 (see FIGS. 5, 12 and 13). Preferably, the jaws are aligned in the slots with the aid of precision alignment pins 74 and associated holes in the jaws 34 and the jaw holders. With this arrangement, the bearing blocks 30 on either side of the pin translate toward and away from the bearing pin with the respective jaw holder assemblies.

Figure 6:
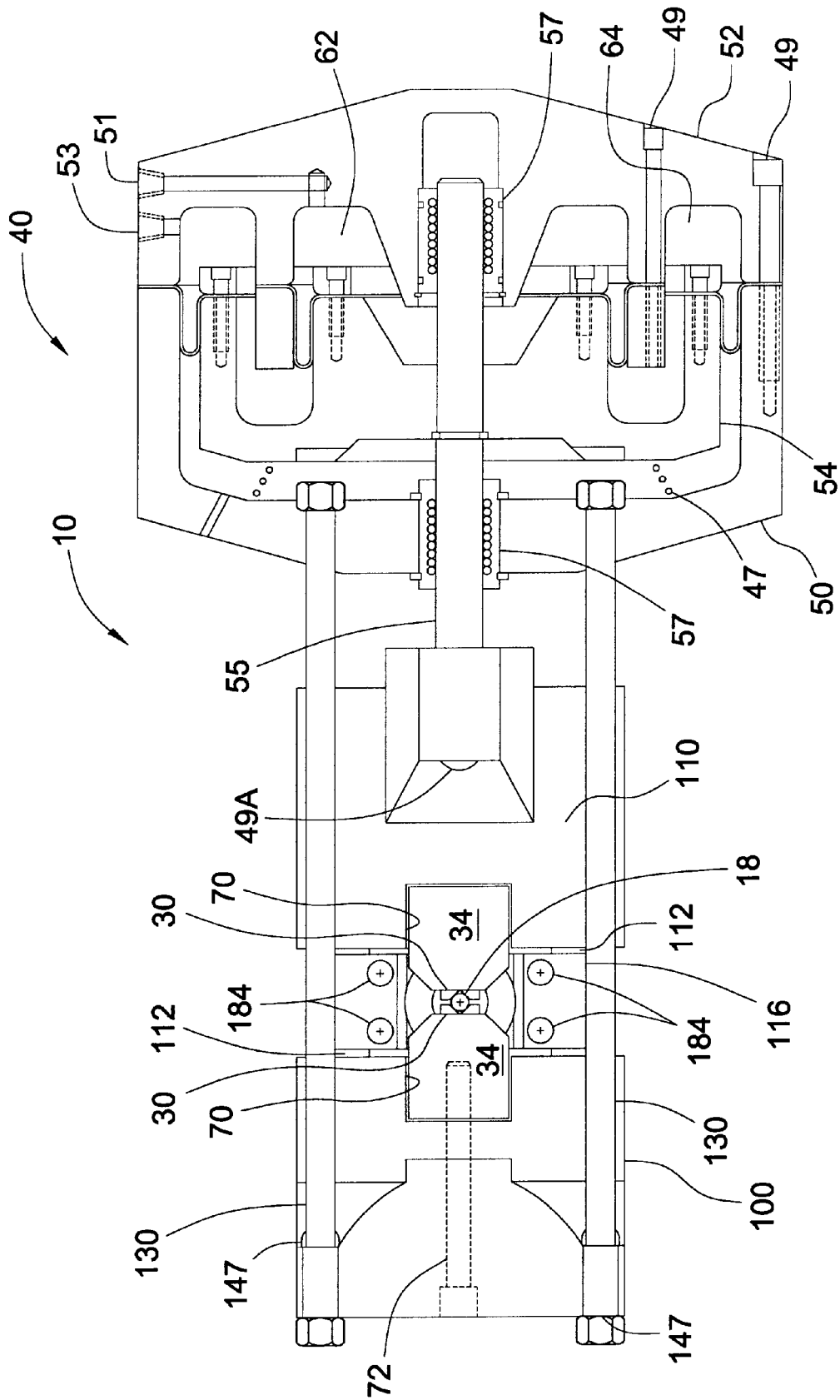

In further carrying out the invention, the jaw holders 100, 110 are uniquely connected to the actuator assembly for back and forth, low-friction, linear floating motion, for applying a load between the pin 18 and the bearing blocks 30. To this end, the jaw holders carry linear bearings 65 for low friction movement on guide rods 112, and the guide rods are clamped into fixed position on the machine in a load pivot housing 116 which is connected to the spindle housing 118 as further described below. The right jaw holder assembly 110 is connected to the actuator piston rod 55 with a screw 49A (FIG. 4) or other mechanical attachment means such that the right jaw holder assembly translates on the guide rods 72 with the piston assembly. And as best seen in FIG. 6, the left jaw holder assembly 100 is connected to the actuator housing 50 with threaded pull rods 130 such that the left jaw holder assembly translates on the guide rods 112 with the actuator housing. In other words, the guide rods 112 are fixed to the machine spindle housing, the left jaw assembly and the actuator housing are connected to translate together on the guide rods, and the right jaw holder and the actuator piston are connected to translate together on the guide rods independently of the actuator housing.

With this arrangement, and as shown in FIG. 6, as air pressure is introduced into either the low pressure chamber 62, or both the low pressure chamber and the high pressure chamber 64 in the actuator 40, the piston 54 and actuator cap 52 move away from one another since neither the piston or the cap is "grounded to the machine, and the jaw holder assemblies 100, 110 translate toward one another as the piston and cap separate, causing pressure to be applied to the bearing pin 18 by the opposing bearing blocks 30. Thus, the pressure between the pin and the bearing blocks is directly related to the pressure supplied to the actuator, and is independent of the position of the bearing blocks, or the wear between the pin and the bearing blocks, and thus can be directly calculated. Further, the load bearing force will not change as a result of wear of either the bearing blocks or the pin, since the pressure is a function of the pressure in the actuator, not the position of the actuator or bearing blocks. With the use of a conventional open-loop pressure regulator, and/or standard regulation and control feedback technology, it is apparent that the accuracy of the loading pressure between the pin and bearing blocks is easily controlled and predictable, providing for constant, controlled increasing or decreasing, or other desired loading conditions. Advantageously, de-coupling the actuator from direct connection or grounding to the frame of the machine as contemplated herein grounds the piston/actuator mechanism through the pin, and insures equal and opposite loading on the pin by the bearing blocks. In other words, de-coupling the actuator from the frame of the machine provides for a unique floating, automatically self-centering, loading mechanism. Further, to eliminate side-loading on the pin, the center of the piston, the piston-housing, and the guide-rod are aligned with the center of the bearing blocks, as best seen in FIG. 4, and with the center of the pin, as best seen in FIG. 6. When pressure is relieved from the actuator, the spring 47 returns the jaw holders to an open position as shown in FIG. 7.

In keeping with the invention, a wear sensor 150 (FIG. 4) is mounted to one of the jaw holder assemblies for measuring the wear that occurs during testing. In the embodiment shown, as LVDT 158 is connected the left jaw holder 100, and the plunger 152 of the LVDT is magnetically (or otherwise) coupled to rod 154 which is, in turn, fixedly connected (not shown) or grounded to the spindle housing 118 or other fixed structure of the machine through member 156. With this arrangement, the body of the LVDT 158 moves with the jaw assembly 100, and provides an electric output signal based on such movement relative to the stationary plunger 152. This output signal is then calibrated and electronically processed to provide a digital read-out or recording of the dimensional movement of the jaw during the testing, and thus a direct indication of the radial wear occurring during the test.

In further keeping with the invention, the load pivot housing 116 is operably coupled with a torque sensing apparatus such as a force transducer 126 for measuring the torque produced by the friction between the rotating pin 18 and the bearing blocks 30, another indicator of the lubrication properties being tested. As best seen in FIGS. 8–11, the load pivot housing 116 includes an upper body portion 180 and leg portions 182 extending downwardly on opposite sides of the spindle 16 (FIG. 4), and for further identification purposes in the drawings, includes internal or radially inwardly facing surfaces 193. Each guide rod 112 is slidably received in an opening in each leg 182 (FIG. 8), and is clamped therein with screws 184. The load pivot housing 116 is rotatably carried on a load pivot mount 119 (FIG. 4) with ball bearings 186, and the load pivot mount is connected to the spindle housing 118 with bolts 120. Thus the guide rods, load pivot housing, and the entire actuator assembly are fixed laterally with respect to the spindle housing, but advantageously rotate relative to the spindle housing during a test as torque is developed between the bearing blocks and the rotating pin.

The load pivot housing 116 also includes an arm 220 (FIG. 8) extending radially outwardly from the upper body portion 180. The force transducer 126 is then mounted between the arm 220 and the frame 12 of the machine. With the force transducer acting over a know "lever arm", i.e., the distance between the center of the spindle and the end of the arm, the output signal from the force transducer is calibrated and electronically processed for displaying or recording the torque generated by friction during a test. Preferably, the force transducer is mounted with ball-socket type joints 230 that provide for freedom of movement in three dimensions. Advantageously, a second arm 225 can be included on the load pivot housing 116 to aid in calibrating the force transducer 126 by applying a known weight over the same lever arm length, or for ease of checking the calibration of the transducer on a machine in a laboratory.

Figure 15:
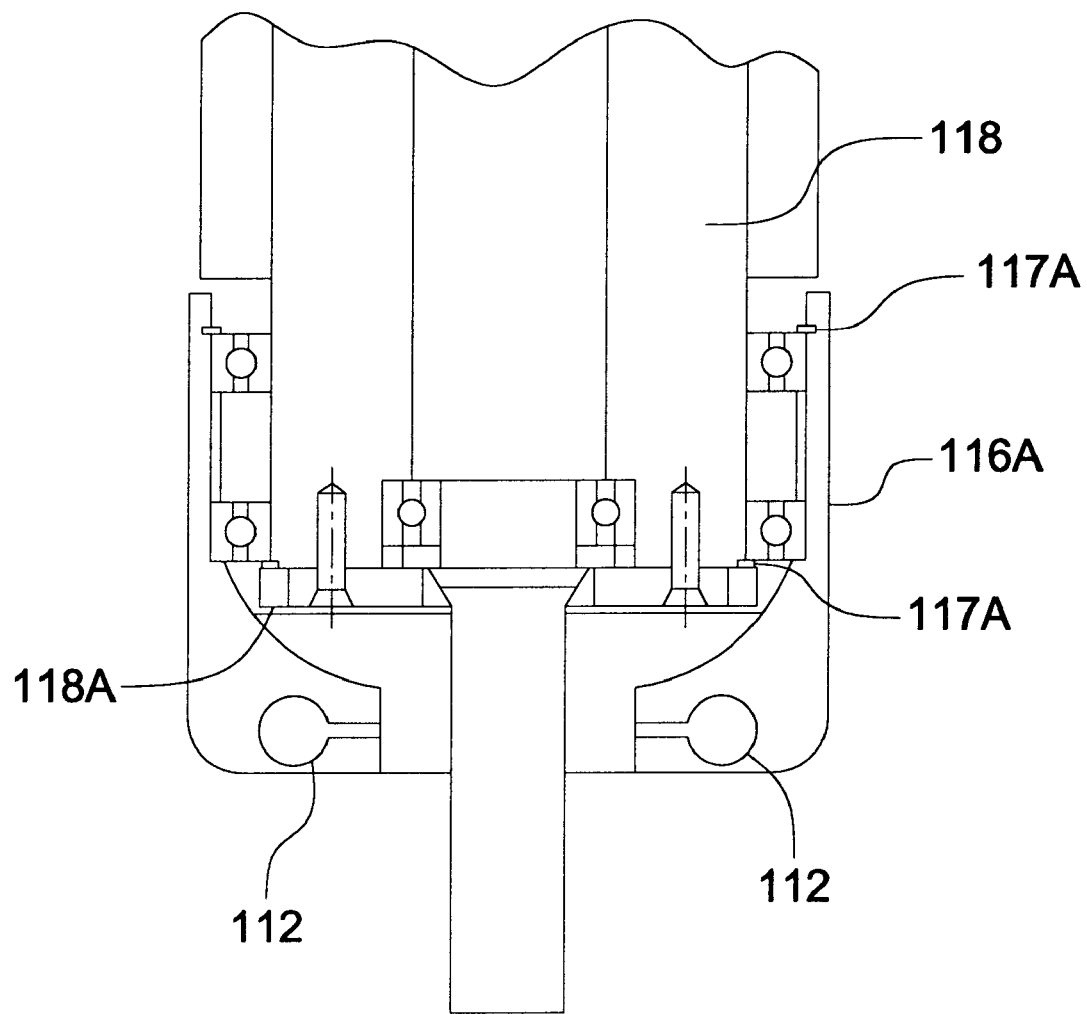
FIG. 15 is a partial cross-sectional view of an alternate embodiment of certain parts shown in FIG. 4.

It will be apparent to those skilled in the art that to actuator-load generating apparatus, the wear sensing apparatus, and the torque sensing apparatus, may be alternately configured and alternately mounted while remaining within the scope of the present invention. By way of example only, in an alternate embodiment shown in FIG. 15, the load pivot housing 116A is configured and adapted for mounting to the spindle housing 118 to reduce the length between the spindle housing and the bearing pin 18. In this instance, retaining rings 117A and a collar 118A connected with screws secure the load pivot housing 116A for rotation relative to the spindle housing. And in another alternate embodiment (not shown) the load pivot housing 116 is replaced with functionally equivalent structure fixed to the machine frame for carrying the guide rods 112 generally as shown. In this instance, the torque generated between the bearing blocks 30 and the rotating pin 18 is detected with, for example, a torque sensing strain gauge mounted to the spindle shaft 16.

Alternate force generating and transmission actuator devices may also be utilized within the scope of the present invention. By way of example only, it will be apparent to those skilled in the art that the actuator need not contain the high and low pressure chambers, but a single-chamber actuator may be utilized. Alternately, the actuator may utilize other sources of power such as a hydraulic actuator or an electrically powered actuator. These and other alternate embodiments are clearly encompassed within the scope of the present invention.

From the foregoing, it will further be apparent that the present invention brings to the art a unique arrangement for loading test specimens during material wear and lubrication testing. By virtue of the mounting arrangement of the bearing block holders 100, 110 on the guide rods 112, permitting free sliding relative to the housing 12 of the machine, and the unique connection arrangement between the bearing block holders and the actuator 40, such that the actuator is not fixed relative to the housing, applying pressure to the actuator results in an automatic self-centering action resulting in equal and opposite pressure being applied between the bearing blocks 30 and the wear pin 18, completely independent of the wear that may occur, and independent of any other physical constraints. Further, the low-friction linear-acting actuator permits controlled, repeatable loading conditions for different tests. In addition, the unique floating arrangement of the bearing block holders and actuator permits direct measurement of wear and torque generated during the testing.

I claim:

1. A machine adapted to test material wear and lubrication properties, said machine comprising:

a frame;

a first wear member connected to said frame;

a guide connected to said frame;

a pair of holders slidably connected to said guide for linear sliding movement toward and away from said first wear member between first and second positions;

a pair of second wear members carried in said holders and positioned such that said second wear members are brought into oppositely directed contact with said first wear member for conducting a test as said holders approach one of said positions; and force transmission means for simultaneously sliding said holders along said guide toward said one position, said force transmission means being connected to said holders for movement therewith with respect to said guide and independently of said frame.

2. A machine as defined in claim 1 in which said force transmission means is operative between said positions, said machine further comprising means for selectively moving said force transmission means between said positions.

3. A machine as defined in claim 2 in which said force transmission means includes first and second force transmitting members (i) movable between said positions, (ii) coupled together for movement in opposite directions upon moving between said positions, and (iii) connected to respective ones of said holders for sliding said holders toward and away from one another.

4. A machine as defined in claim 3 in which said force transmission means is a dual-acting actuator mechanism having said first and second force transmitting members responsive to a single operating power source for driving said parts in opposite directions.

5. A machine as defined in claim 4 in which said force transmission means includes a pressure responsive piston-type actuator having a housing member, a piston member movable therein, and a pressure chamber defined therebetween such that said piston member and said housing member move in opposite directions as pressure is introduced into said chamber, said piston member being connected to one of said holders and said housing member being connected to the other of said holders.

6. A machine as defined in claim 1 in which said holders are disposed on opposite sides of said first wear member.

7. A machine as defined in claim 1 further comprising means for detecting linear motion operably coupled between one of said holders and the frame for measuring the movement of said holder during a test.

8. A machine adapted to test material wear and lubrication properties, said machine comprising:

a frame;

a first wear member connected to said frame;

a guide connected to said frame;

a pair of holders disposed on opposite sides of said first wear member and slidably connected to said guide for sliding movement toward and away from said first wear member independently of the frame;

a pair of second wear members carried in said holders and positioned such that said second wear members are brought into opposing contact with said first wear member for conducting a test as said holders approach one another;

an actuator mechanism having first and second actuator parts linearly movable between first and second positions, said actuator parts moving in opposite directions when moving between said positions;

means for connecting (i) said first actuator part with one of said holders for movement therewith with respect to said guide and (ii) said second actuator part with the other of said holders for movement therewith with respect to said guide, such that said holders recede from one another as said actuator parts move toward one of said positions and such that said holders approach one another for conducting the test as said actuator parts move toward the other of said positions, and means for actuating said actuator parts toward said other position.

9. A machine as defined in claim 8 in which said actuator mechanism is a dual-acting actuator mechanism having first and second actuator parts responsive to a single operating power source for driving said parts in opposite directions.

10. A machine as defined in claim 9 in which said actuator mechanism includes a pressure responsive piston-type actuator having a housing member, a piston member movable therein, and a pressure chamber defined therebetween such that said piston member and said housing member move in opposite directions as pressure is introduced into said chamber, said piston member being connected to one of said holders and said housing member being connected to the other of said holders.

11. A machine as defined in claim 10 in which said holders approach one another as said first and second actuator parts recede from one another.

12. A machine as defined in claim 8 further comprising means for detecting linear motion operably coupled between one of said holders and the frame for measuring the movement of said holder during a test.

13. A machine adapted to test material wear and lubrication properties, said machine comprising:

a frame;

a first wear member connected to said frame and extending generally along a first axis;

a guide connected to said frame;

a pair of holders disposed on opposite sides of said first wear member and slidably connected to said guide for sliding movement in a direction generally perpendicular to said axis toward and away from said first wear member independently of the frame;

a pair of second wear members carried in said holders and positioned such that said second wear members are a brought into opposing contact in said generally perpendicular direction with said first wear member for conducting a test as said holders approach one another; and a pressure responsive dual-action piston-type linear-motion actuator having a housing member, a piston member movable therein, and a pressure chamber defined therebetween and positioned such that said piston member and said housing member move in opposite directions in said generally perpendicular direction as pressure is introduced into said chamber, said piston member being connected to one of said holders and said housing member being connected to the other of said holders for moving said holders toward and away from said first wear member.

14. A machine adapted to test material wear and lubrication properties, said machine comprising:

a frame;

a first wear member connected to said frame and extending generally along a first axis;

a guide connected to said frame for rotation about said first axis;

a pair of holders slidably connected to said guide for sliding movement toward and away from said first wear member between first and second positions independently of said frame;

a pair of second wear members carried in said holders and positioned such that said second wear members are brought into oppositely directed contact with said first wear member for conducting a test as said holders approach one of said positions;

force transmission means for simultaneously sliding said holders along said guide toward said one position, said force transmission means being connected to said holders for movement therewith with respect to said guide and independently of said frame; and means for detecting rotary motion operably coupled between said guide and the frame for detecting at least one of the motion and torque applied to said guide during a test.

15. A machine adapted to test material wear and lubrication properties, said machine comprising:

a frame;

a first wear member connected to said frame and extending generally along a first axis;

a guide connected to said frame for rotation about said first axis;

a pair of holders disposed on opposite sides of said first wear member and slidably connected to said guide for sliding movement toward and away from said first wear member independently of the frame;

a pair of second wear members carried in said holders and positioned such that said second wear members are brought into opposing contact with said first wear member for conducting a test as said holders approach one another;

an actuator mechanism having first and second actuator parts movable between first and second positions, said actuator parts moving in opposite directions when moving between said positions;

means for connecting (i) said first actuator part with one of said holders for movement therewith with respect to said guide and (ii) said second actuator part with the other of said holders for movement therewith with respect to said guide, such that said holders recede from one another as said actuator parts move toward one of said positions and such that said holders approach one another for conducting the test as said actuator parts move toward the other of said positions;

means for actuating said actuator parts toward said other position; and means for detecting rotary motion operably coupled between said guide and the frame for detecting at least one of the motion and torque applied to said guide during a test.

* * * * *